United States Patent
Kim et al.

(10) Patent No.: US 11,168,106 B1
(45) Date of Patent: Nov. 9, 2021

(54) SYNTHESIS AND STABILIZATION OF NICOTINAMIDE RIBOSE AND ITS DERIVATIVES

(71) Applicants: Hyo-Joong Kim, Gainesville, FL (US); Steven A Benner, Gainesville, FL (US); Ion Mircesti Scorei, Craiova (RO)

(72) Inventors: Hyo-Joong Kim, Gainesville, FL (US); Steven A Benner, Gainesville, FL (US); Ion Mircesti Scorei, Craiova (RO)

(*) Notice: Subject to any disclaimer, the term of this patent is extended or adjusted under 35 U.S.C. 154(b) by 0 days.

(21) Appl. No.: 16/160,189

(22) Filed: Oct. 15, 2018

Related U.S. Application Data

(60) Provisional application No. 62/592,653, filed on Nov. 30, 2017.

(51) Int. Cl.
C07H 19/048 (2006.01)
C07H 1/02 (2006.01)

(52) U.S. Cl.
CPC ............ C07H 19/048 (2013.01); C07H 1/02 (2013.01)

(58) Field of Classification Search
CPC ........................... C07H 19/048; C07H 11/04
USPC ...................................................... 536/26.8
See application file for complete search history.

(56) References Cited

FOREIGN PATENT DOCUMENTS

CN 102605026 A * 7/2012

OTHER PUBLICATIONS

Hyo-Joong Kim et al. (Proceedings of the National Academy of Sciences of the United States of America (2017), 114(43), 11315-11320).*
Parca et al. (Nov. 2012 | vol. 7 | Issue 11 | e50240, 1-12).*
Tao et al.; CN 102605026 A; Jul. 25, 2012 (Machine—English Translation).*
Sharma et al. (Ind J Clin Biochem (Jul.-Sep. 2014) 29(3):269-278).*
Kim et al. (Journal of mass spectrometry: JMS, (Jun. 2003) vol. 38, No. 6, pp. 632-640).*

* cited by examiner

*Primary Examiner* — Shaojia A Jiang
*Assistant Examiner* — Michael C Henry

(57) ABSTRACT

Nicotinamide ribose has many applications, including as a dietary supplement. This invention convers a process to prepare nicotinamide ribose it in its phosphorylated form. The instant invention is based on the discovery that nicotinamide ribose phosphate emerges in stable form by direct reaction of ribose-1,2-cyclic phosphate. It is based on the further conversion of the phosphorylated nicotinamide ribose product to unphosphorylated nicotinamide ribose upon treatment with an enzymatic phosphatase, most preferably in buffer containing borate. It is based on the further discovery that compositions of nicotinamide ribose with borate slow the decomposition of nicotinamide ribose, and therefore is more useful than compositions of nicotinamide ribose without borate.

9 Claims, 4 Drawing Sheets

US 11,168,106 B1

SYNTHESIS AND STABILIZATION OF NICOTINAMIDE RIBOSE AND ITS DERIVATIVES

CROSS REFERENCE TO RELATED APPLICATIONS

This non-provisional application claims benefit to provisional U.S. patent application 62/592,653 filed 30 Nov. 2017 for "A Simple Synthesis of Nicotinamide Ribose Phosphate."

STATEMENT OF RIGHTS TO INVENTIONS MADE UNDER FEDERALLY-SPONSORED RESEARCH

None.

THE NAMES OF PARTIES TO A JOINT RESEARCH AGREEMENT

Not applicable

INCORPORATION BY REFERENCE OF MATERIAL SUBMITTED ON A COMPACT DISK

None

BACKGROUND OF THE INVENTION

1. Field of the Invention

This invention relates the synthesis and stabilization of nicotinamide ribose and nicotinamide riboside derivatives, specifically nucotinamide ribose 5'-phosphate.

2. Description of the Related Art

Nicotinamide ribose is widely used as a food additive, being a part of the cofactor nicotinamide adenine dinucleotide, a vestige of the "RNA world" [Gilbert, W. *Nature* 1986, 319, 618] that remains widespread throughout modern life [White III, H. B. *J. Mol. Evol.* 1976, 7, 101-104]. Nicotinamide ribose has special reactivity. Its glycosidic bond attaches a positively charged pyridinium heterocycle to a carbohydrate. This bond is therefore especially unstable to cleavage, making the molecule and its derivatives difficult to synthesize. This creates broad utility for any method for the synthesis of nicotinamide ribose and its synthesis.

Nicotinamide ribose has been suggested to be useful as a dietary supplement in a number of clinical studies [Dollerup et al. (2018) *American J. Clinical Nutrition* 108, 343-353]. It is sold under various trademarks (e.g. example, Tru Niagen™), and is suggested to elevate the level of nicotinamide adenine dinucleotide in those who consume it [Martens et al. (2018). *Nature Comm.* 9:1286]. These studies report that chronic nicotinamide riboside supplementation is well-tolerated and elevates NAD in healthy middle-aged and older adults. Other studies suggest oral bioavailability in mice and humans [Trammell et al. (2016). *Nature Comm,* 7:12948.]

Unfortunately, current procedures for manufacturing nicotinamide ribose are expensive. Further, nicotinamide ribose is itself unstable. When analyzed by HPLC and other standard analytical methods show that many samples of commercial nicotinamide ribose are in fact mixtures of products that indicate decomposition of the material.

BRIEF SUMMARY OF THE INVENTION

The instant invention is based on the discovery that nicotinamide ribose phosphate emerges in stable form by direct reaction of ribose-1,2-cyclic phosphate. Ribose-1,2-cyclic phosphate is available inexpensively from ribose and amidotriphosphate, which is available from the very inexpensive starting materials cyclic trimetaphosphate and ammonia. It is based on the further conversion of the phosphorylated nicotinamide ribose product to unphosphorylated nicotinamide ribose upon treatment with an enzymatic phosphatase. It is based on the further discovery that the nicotinamide ribose can be stabilized by borate.

DETAILED DESCRIPTION OF THE INVENTION

Figure 1:
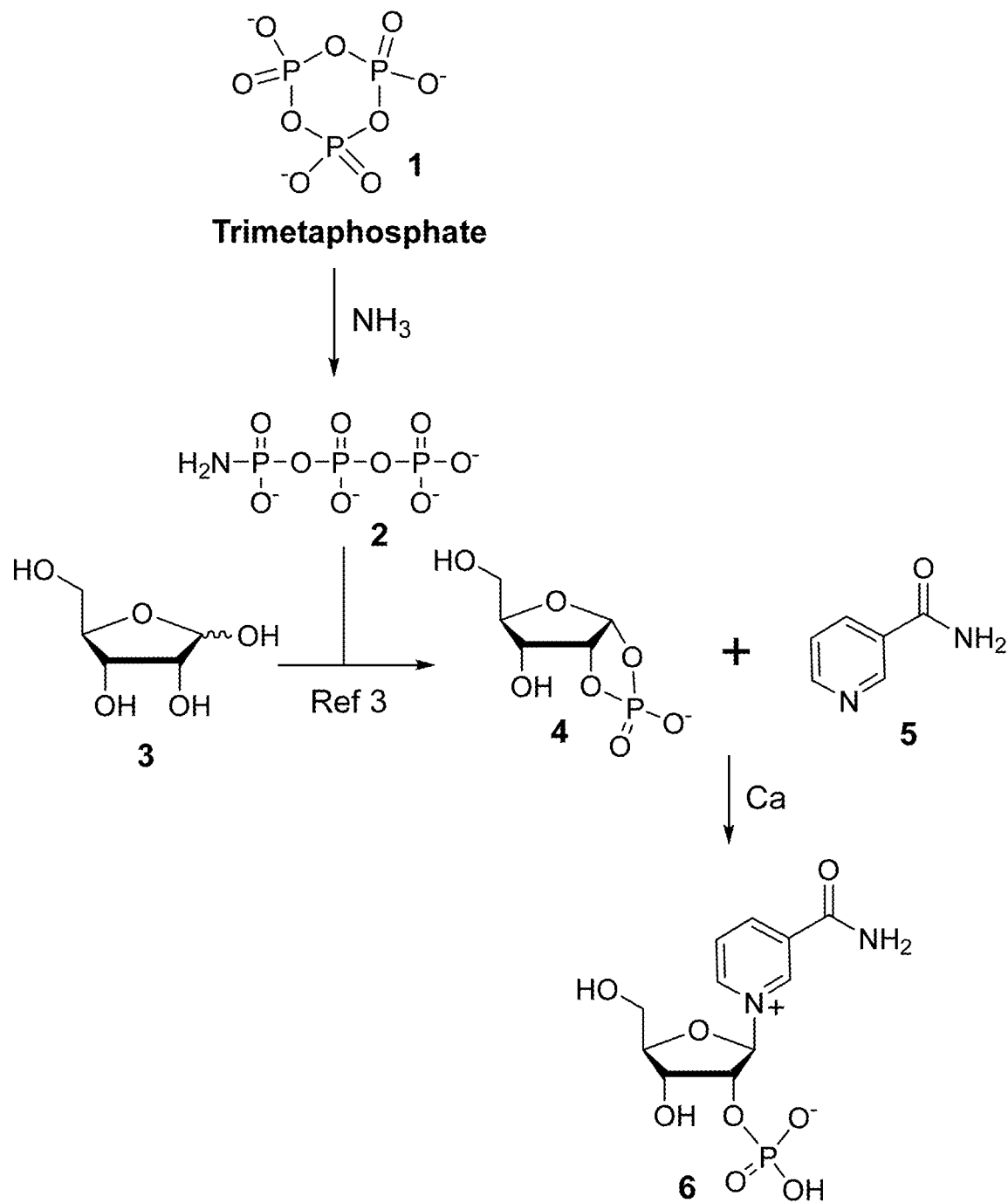
FIG. 1. The chemical pathway to nicotinamide ribose 2'-phosphate 6. Nicotinamide ribose 2'-phosphate emerges from the coupling reaction of ribose-1,2-cyclic phosphate 4 and nicotinamide 5. 4 is available from ribose 3 and amidotriphosphate 2. Amidotriphosphate 2 comes from the reaction of ammonia and trimetaphosphate 1.

The instant invention is based on the discovery that nicotinamide ribose phosphate emerges in stable form by direct reaction of ribose-1,2-cyclic phosphate 4 (FIG. 1) and nicotinamide 6 in the presence of Ca$^{2+}$ (FIG. 1) [Kim, H.-J., Benner, S. A. *Proc. Natl. Acad. Sci. U.S.A.* 2017, 114, 11315-11320.]. Ribose-1,2-cyclic phosphate 4 is available inexpensively from ribose 3 and amidotriphosphate 2, which is available from the very inexpensive starting materials trimetaphosphate 1 and ammonia [Krishnamurthy, R., Guntha, S., Eschenmoser, A. *Angew. Chem. Int. Ed.* 2000, 39, 2281-22851. It is based on the further discovery that the product can be converted to nicotinamide ribose upon treatment with an enzymatic phosphatase. It is based on the further discovery that the nicotinamide ribose can be stabilized by borate.

Figure 2:
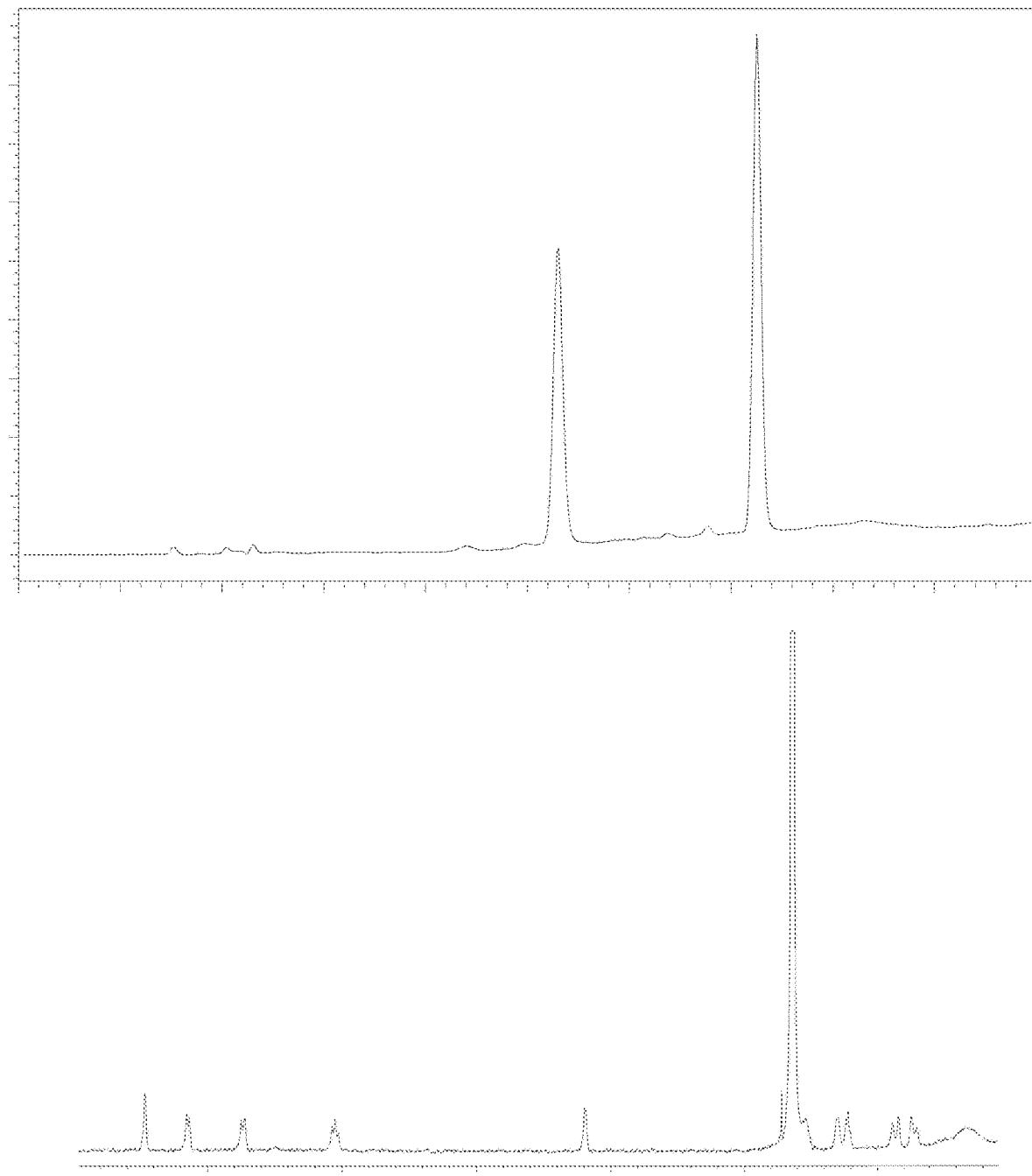
FIG. 2. Formation of nicotinamide ribose phosphate 6. (A) HPLC profile of the formation of nicotinamide ribose 2'-phosphate 6 from the coupling reaction of 4 and 5. (B)$^{1}$H NMR spectrum of nicotinamide ribose 2'-phosphate 7 shows 4 protons in aromatic region (8~10 ppm) and 5 protons in ribose region (3~5 ppm) and one proton in nucleosidic anomeric region (6~7 ppm).

In detail (FIG. 1), a mixture of ribose-1,2-cyclic phosphate 4, nicotinamide 6 and calcium chloride in aqueous solution is most preferably dried by heating (with continued heating; no intervention is needed immediately after the water has been lost) at 90° C. for 3 hours. The mixture is then, under a presently preferred procedure, re-dissolved in water and analyzed by reverse phase HPLC-UV. Nicotinamide ribose 2'-phosphate 7 was recovered in this procedure (17.7% yield) together with unreacted nicotinamide 6 (FIG. 2, Table 1). Under the same conditions, adenine ribose 2'-phosphate is made from adenine and the same phosphate precursor [Krishnamurthy et al., op. cit.]. The structure of 6 was proven by UV spectroscopy, high resolution mass analysis, and ¹H NMR spectroscopy.

Remarkably, the yield of the coupling reaction increased to 30~35% when ammonium formate was added. Table 1 and Table 2 collect data showing how the outcome of the reaction depended on various experimental parameters. The coupling reaction was also discovered to be efficient at temperatures as low as 45° C. This comprises the presently preferred embodiment of the instant invention.

The coupling reaction is stereoselective, giving only the desired beta-nucleoside, as shown by HPLC. Without wishing to be bound by theory, the stereoselectivity of the coupling reaction may be rationalized by noting that the cyclic phosphate, which activates the 1'-position of the ribose, blocking the alpha-face of the ribose in the same time and shows same stereoselectivity in purine nucleotide synthesis.

This phosphate is readily separated from unreacted nicotinamide by chromatography, ion exchange chromatography, or solvent extraction, as is well known in the art. Similar procedures allow removal of the unreacted ribose phosphate.

This phosphate is readily converted to nicotinamide ribose by treatment with an enzymatic phosphatase in aqueous solution, which may contain buffer, including buffers containing borate. The presently preferred phosphatase is alkaline phosphatase. This treatment does not decompose the nicotinamide ribose, and does not changes its stereochemistry.

The nicotinamide ribose generated by removal of the phosphate group has a 1',2'-diol unit that is believed to bind to borate, in other nucleosides [Weser (1967). Chelation of boric acid with some nucleosides. Z Naturforsch B 22, 457-458; Kim et al. (2016) Evaporite borate-containing mineral ensembles make phosphate available and regiospecifically phosphorylate ribonucleosides. *Angew. Chem. Int. Ed.* 55, 1-6] and in nicotinamide adenine dinucleotide [Johnson & Smith (1977). Nucleophile and borate reactivity with nicotinamide adenine dinucleotide and its analogues. *J. Org. Chem.* 42, 2580-2589; Johnson & Smith (1977). The interaction of borate and sulfite with pyridine nucleotidest. *Biochemistry* 15, 553-559]. The instant invention is based on the discovery that borate stabilizes nicotinamide ribose with respect to decomposition. Without wishing to be bound by theory, this may be attributed to the formation of a complex between borate and the 1,2-diol unit of nicotinamide ribose.

EXAMPLES

Example 1

Analytical Methods

High-performance liquid chromatography (HPLC) analysis was done with a C-18 reversed-phase narrow bore column (3 mm i.d., 150 mm length, 5 μm; SunFire; Waters) on a Waters 2695 separation module equipped with 996 photodiode array detector. The column was eluted with a gradient of (A) aqueous 25 mM triethylammonium acetate and (B) 100% acetonitrile. The elution program created a linear gradient started from 100% (by volume) A to 85% A at 10 min with flow rate of 0.5 mL/min. Peak detection and integration were conducted with the signal at 260 nm. Full UV spectra (230~400 nm) were also obtained. Preparative HPLC purification was done using an ion exchange column (22 mm id, 250 mm length, 5 μm; DNAPac PA-100; Thermo Fisher Scientific) on a Waters Delta 600 module. The column was eluted with a gradient of (A) water and (B) 1 M ammonium bicarbonate. The elution program created a linear gradient started from 100% A to 70% A at 15 min with flow rate of 10 ml/min. Peak detection was conducted using the 260 nm absorbance. ¹H NMR spectra were recorded in deuterium oxide on Varian Mercury 300 NMR spectrometer. High resolution mass spectrometry was conducted on Agilent 6220 Time-of-Flight connected with Agilent 1100 series system consisting of G13793 degasser and G1312B binary pump with Electro spray ionization in negative mode.

Nicotinamide Ribose 2'-phosphate (6)

Ribose-1,2-cyclic phosphate 4 was prepared following the literature.[3] The reaction of 4 and nicotinamide 5 was conducted in an Eppendorf tube containing ribose 1,2-cyclic phosphate 4 (5 μL, 3.75 mM), nicotinamide 5 (5 μL, 15 mM) and calcium chloride (15 μL, 15 mM) in aqueous solution with specified amount of ammonium formate. The mixture was dried by heating (with further heating) at specified temperature for specified time. It was re-dissolved in water (0.3 mL) and analyzed by reversed-phase HPLC with 20 μL of injection. The yield was calculated based on the amount of starting nicotinamide and shown in Table 1 and Table 2. The preparative scale synthesis of 6 was conducted with an aqueous mixture containing nicotinamide 5 (7.5 mM, 0.4 mL), ribose 1,2-cyclic phosphate 4 (15 mM, 0.4 mL), and $CaCl_2$ (15 mM, 1.2 mL). The mixture was dried and heated at 90° C. for 3 hours. It was dissolved in water (6 mL) and purified on reverse phase prep HPLC to give syrup after lyophilization (~0.15 mg, 15% based on nicotinamide). ¹H-NMR (300 MHz, $D_2O$) δ=9.45 (s, 1H), 9.14 (d, J=5.4, 1H), 8.73 (d, J=7.8, 1H), 8.05 (t, J=6.6, 1H), 6.20 (s, 1H), 4.2~4.4 (m, 2H), 3.6~4.0 (m, 3H). HRMS (ESI⁻): calc. for: $[C_{11}H_{14}N_2O_8P]^-$ 333.0493, found: 333.0493 [M-H]⁻.

The yield of the coupling reaction was determined by the peak integration of the product compared with the integration of commercial sample of nicotinamide ribose 5'-phosphate (Sigma-Aldrich). An aqueous solution of commercial nicotinamide ribose 5'-phosphate (5 μL, 3.75 mM) was diluted in water to make total volume of 0.3 mL. This solution was analyzed by reversed-phase HPLC with 20 μL of injection. The integration of the peak at 2.5 min at 260 nm is 473,000 and this number was used for the determination of the yield of the coupling reaction to give compound 6.

The amount of the unreacted starting material (nicotinamide 5) was determined by the peak integration of the peak at 7.2 min compared with the integration of HPLC injection of nicotinamide. Specifically an aqueous solution of nicotinamide (5 μL, 3.75 mM) was diluted in water to make total volume of 0.3 mL. This solution was analyzed by reversed-phase HPLC with 20 μL of injection. The integration of the peak at 7.2 min at 260 nm is 388,500 and this number was used for the determination of the amount of the unreacted nicotinamide 5.

The phosphate can be removed by incubating the product in an aqueous solution containing a phosphatase, preferably alkaline phosphatase, by a process well known in the art.

TABLE 1

Formation of nicotinamide ribose phosphate 6 with varying amounts of ammonium formate. A mixture of ribose 1,2-cyclic phosphate 4 (5 µL, 3.75 mM), nicotinamide 5 (5 µL, 15 mM) and calcium chloride (15 µL, 15 mM) and variable amounts of ammonium formate (15 mM) in aqueous solution was dried by heating (with further heating) at 90° C. for 3 hours

|   | Ammonium Formate (15 mM) | Yield of 7 (%) | Recovered Nicotinamide (%) |
|---|---|---|---|
| 1 | 0 µL | 17.7 | 93.1 |
| 2 | 2.5 µL | 20.9 | 80.9 |
| 3 | 5 µL | 22.2 | 78.9 |
| 4 | 7.5 µL | 30.0 | 69.0 |
| 5 | 10 µL | 30.6 | 69.3 |
| 6 | 12.5 µL | 31.0 | 67.8 |

TABLE 2

Formation of nicotinamide ribose phosphate 6 at lower temperature. A mixture of ribose-1,2-cyclic phosphate 4 (5 µL, 3.75 mM), nicotinamide 5 (5 µL, 15 mM) and calcium chloride (15 µL, 15 mM) and ammonium formate (6 µL, 15 mM) in aqueous solution was dried by heating (with further heating) at 45° C. and 55° C.

|   | Temperature | Reaction time | Yield of 7 (%) |
|---|---|---|---|
| 1 | 45° C. | 4 hrs | 4.5 |
| 2 | 45° C. | 1 day | 22.7 |
| 3 | 45° C. | 2 days | 30.7 |
| 4 | 45° C. | 3 days | 35.7 |
| 5 | 55° C. | 4 hrs | 17.5 |
| 6 | 55° C. | 1 day | 33.4 |
| 7 | 55° C. | 2 days | 33.7 |
| 8 | 55° C. | 3 days | 30.3 |

These results show that the nucleosidic bond in NAD can be easily made from ribose-1,2-cyclic phosphate and nicotinamide. Here, we combine the mild temperature (as low as 45° C.) in dry conditions, with $Ca^{2+}$ and ammonium formate from HCN, the high yield (~35%) and stereoselectivity is suitable for the production of nicotinamide ribose phosphate.

Example 2. Stabilization of Nicotinamide Ribose by Borate

Analytical Methods

Liquid chromatography was done with a 1525 Binary HPLC Pump, using the Empower 3 data system. The mobile phase was acetonitrile at a flow rate of 0.4 mL/min, and an injection volume of 20 µL.

Mass spectrometry was done with an $ESI^+$ ionization mode with capillary voltage of 0.8 eV and a cone voltage of 10.0 V and a probe temperature of 450°. MS Procedures Nicotinamide riboside (NR) as its chloride salt was used at 100 mM. Boric acid: was used at 300 mM. All samples were prepared in water. This, 1 mg/mL of nicotinamide riboside of capsule content was weighed in a 25 mL volumetric flask. Water was added to 25 mL total volume. For the reaction in the presence of boric acid, the same was done with boric acid added in a 1:1 molar ratio.

In either case, 5 mL of each solution prepared was placed in the water bath at 65° C. A control was incubated at room temperature. After incubation for 8 h, 2 µL of each solution (heated and not heated) are placed on the HPTLC plate. The plate is eluted in the following mobile phase: ethanol, ammonium acetate 1 M (7:3). The plate is read at 254 nm to obtain the respective peaks.

TABLE 3

Decomposition of nicotinamide ribose without borate

| Area [%] | Assigned substance |
|---|---|
| 70.1878 | Nicotinamide riboside |
| 29.8122 | Nicotinamide |

TABLE 4

Decomposition of nicotinamide ribose with borate

| Area [%] | Assigned substance |
|---|---|
| 86.07584 | Nicotinamide riboside |
| 13.92416 | Nicotinamide |

Figure 3:
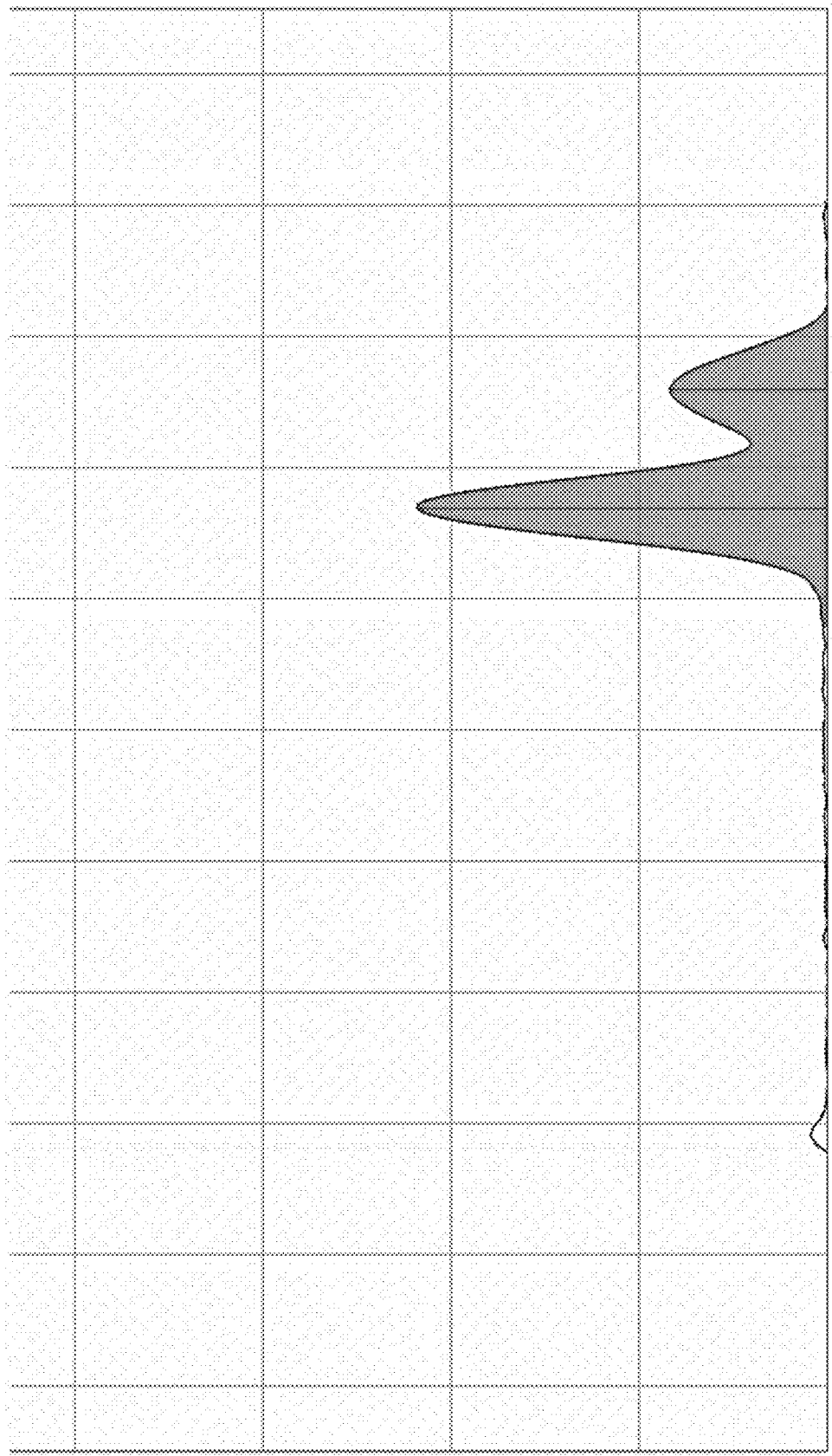
FIG. 3. Decomposition of nicotinamide ribose in the absence of borate.
Figure 4:
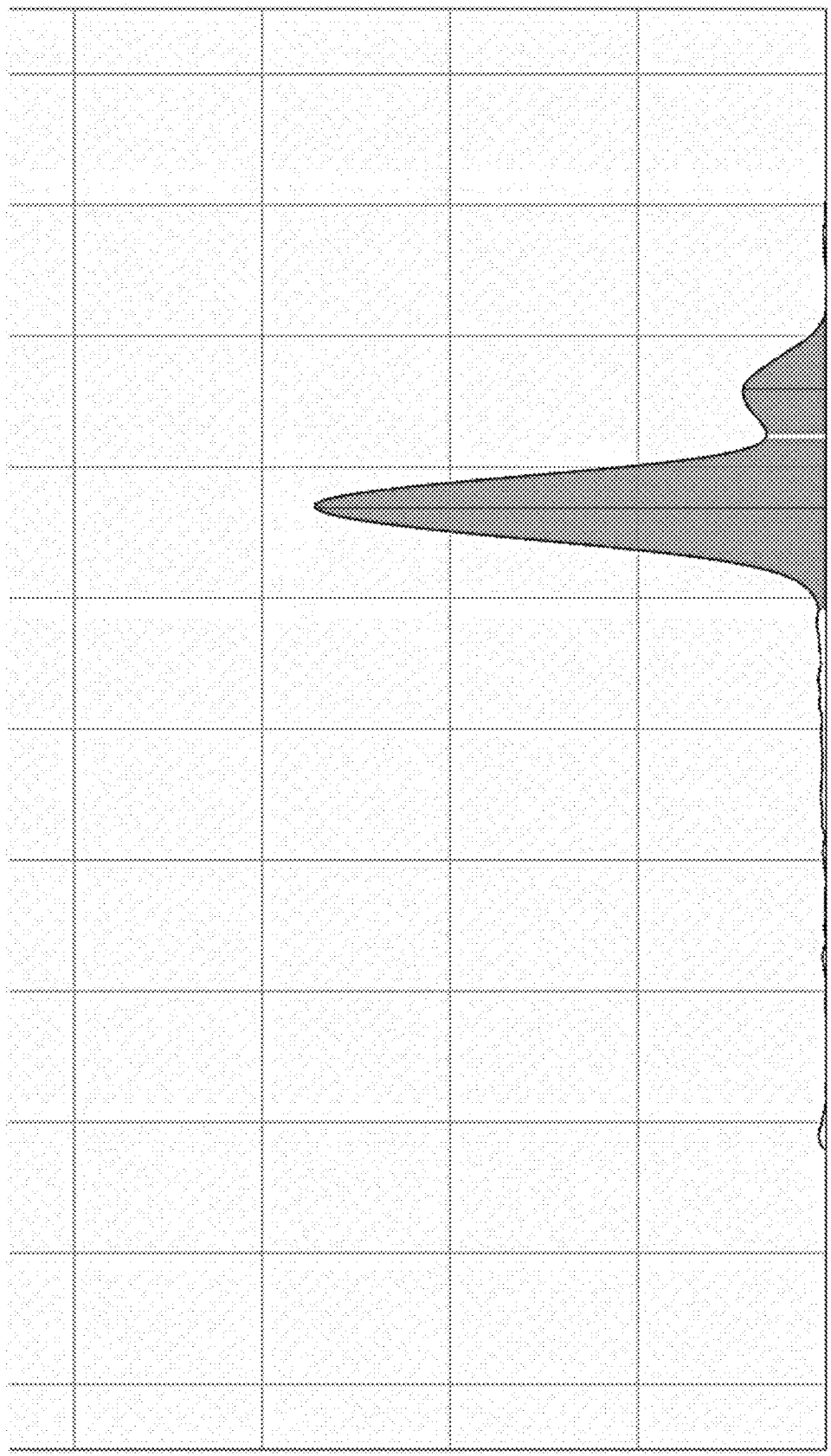
FIG. 4. Decomposition of nicotinamide ribose in the presence of borate.

These results show that nicotinamide ribose is stabilized by boric acid BA (see FIG. 3 and FIG. 4)

What is claimed is:

1. A process for preparing nicotinamide ribose 2'-phosphate, said process comprising mixing an aqueous solution of ribose-1,2-cyclic phosphate with nicotinamide and drying.

2. The process of claim 1, wherein the aqueous solution further contains calcium chloride.

3. The process of claim 1, wherein the aqueous solution further contains ammonium formate.

4. A process for preparing nicotinamide ribose, said process comprising the process of claim 1, followed by a step that contacts the product with a phosphatase in a aqueous solution.

5. The process of claim 4 wherein said aqueous solution includes a buffer.

6. The process of claim 5, wherein said buffer comprises borate.

7. The process of claim 4 wherein said phosphatase is alkaline phosphatase.

8. A composition comprising nicotinamide ribose and borate that produces less than 15% nicotinamide after incubation at 65° C. in water for eight hours.

9. The composition of matter of claim 8 where the molar ratio of nicotinamide ribose to borate is from 1:1 to 1:3.

* * * * *